US008071736B2

(12) United States Patent
Abad et al.

(10) Patent No.: US 8,071,736 B2
(45) Date of Patent: Dec. 6, 2011

(54) NUCLEIC ACID MOLECULES ENCODNG A CATHEPSIN L-LIKE CYSTEINE PROTEASE

(75) Inventors: Andre R. Abad, W. Des Moines, IA (US); Ronald D. Flannagan, Grimes, IA (US); Rafael Herrmann, Wilmington, DE (US); Albert L. Lu, Newark, DE (US); Billy F. McCutchen, College Station, TX (US); James K. Presnail, Avondale, PA (US); Janet A. Rice, Wilmington, DE (US); James F. Wong, Johnston, IA (US); Cao-Guo Yu, Urbandale, IA (US)

(73) Assignees: Pioneer Hi-Bred International, Inc., Johnston, IA (US); E.I. Dupont de Nemours and Company, Wilmington, DE (US)

( * ) Notice: Subject to any disclaimer, the term of this patent is extended or adjusted under 35 U.S.C. 154(b) by 267 days.

(21) Appl. No.: 12/512,425

(22) Filed: Jul. 30, 2009

(65) Prior Publication Data

US 2009/0317891 A1 Dec. 24, 2009

Related U.S. Application Data

(62) Division of application No. 11/949,912, filed on Dec. 4, 2007, now Pat. No. 7,629,449, which is a division of application No. 11/021,115, filed on Dec. 22, 2004, now Pat. No. 7,339,092.

(60) Provisional application No. 60/532,185, filed on Dec. 23, 2003.

(51) Int. Cl.

| | |
|---|---|
| ***C07H 21/04*** | (2006.01) |
| ***C12N 1/20*** | (2006.01) |
| ***C12N 15/63*** | (2006.01) |
| ***C12P 21/00*** | (2006.01) |

(52) U.S. Cl. ................ 536/23.1; 435/320.1; 435/252.3; 435/70.1; 435/71.1

(58) Field of Classification Search ....................... None
See application file for complete search history.

(56) References Cited

U.S. PATENT DOCUMENTS

| | | | |
|---|---|---|---|
| 6,060,594 | A | 5/2000 | English et al. |
| 7,473,821 | B2 | 1/2009 | Abad |
| 2003/0120054 | A1 | 6/2003 | Chen et al. |
| 2004/0096934 | A1 | 5/2004 | Freyssinet et al. |

FOREIGN PATENT DOCUMENTS

| | | | |
|---|---|---|---|
| EP | 0 358 557 | A2 | 3/1990 |
| WO | WO 98/21348 | | 5/1998 |
| WO | WO 02/34774 | A2 | 5/2002 |
| WO | WO 03/018810 | A2 | 3/2003 |
| WO | WO 2004/003148 | A2 | 1/2004 |

OTHER PUBLICATIONS

USPTO in house alignment Seq Id No. 4 vs Q70EX2 from Bown et al, Insect Biochem Mol Biol. Apr. 2004;34(4):305-20 (IDS). Performed May 30, 2011.*
Angsuthanasombat, et al., *J. Biochem. Mol. Biol.*, 2001, pp. 402-407, vol. 34.
Clarke, et al., Physiol. Plant., 2005, pp. 359-361, vol. 123.
De Maagd, et al., *Appl. Environ. Microbiol.*, 1999, pp. 4369-4374, vol. 65.
Guo, et al., *Proc. Natl. Acad. Sci.*, USA, 2004, pp. 9205-9210, vol. 101.
Hill, et al., *Biochem. Biophys. Res. Comm.*, pp. 573-577, vol. 244.
Koiwa, H., et al. "A plant defensive cystain (soycystain) targets cathesin L-like digestive cysteine proteinase (DvCALs) in the larval midgut of western corn rootworm (*Diabrotica virgifera virgifera*)," *FEBS Letters*, 2000, pp. 67-70, vol. 471.
Lazar, et al., *Mol. Cell. Biol.*, 1988, pp. 1247-1252, vol. 8.
Miranda, R., et al. "Processing of Cry 1 Abδ-endotoxin from *Bacillus thuringiensis* by *Manduca sexta* and *Spodoptera frugiperda* midgut proteases: role in protoxin activation and toxin inactivation", *Insect Biochemistry and Molecular Biology*, 2001, pp. 1155-1163, vol. 31.
Moellenbeck, D, J., et al. "Insecticidal proteins from *Bacillus thuringiensis* protect corn from corn rootworms," *Nature Biotechnology*, Jul. 2001, pp. 668-672, vol. 19.
Outchkourov, N, S., et al. "Expression of Sea Anemone Equistatin in Potato. Effects of Plant Proteases on Heterologous Protein Production," *Plant Physiology*, September.
Rukmini, V., et al. "*Bacillus thuringiensis* crystal δ-endotoxin: Role of proteases in the conversion of protoxin to toxin," *Biochimie*, 2000, pp. 109-116, vol. 82.
Tounsi, et al., *J. Appl. Microbiol.*, pp. 23-28, vol. 95.
Bown, D.P., et al. "Characterisation of Cysteine Proteinases Responsible for Digestive Proteolysis in Guts of Larval Western Corn Rootworm (*Diabrotica virgifera*) by Expression in the Yeast *Pichia pastoris," Insect Biochem. Mol. Biol.*, 2004, pp. 305-320, vol. 4.
NCBI Report for Database Accession No. AJ583508.1, From Bown et al, Insect Biochem Mol Biol 2004 34:305-320.
NCBI Report for Database Accession No. AJ583508.1, Alignment with SEQ ID No. 2, From Bown et al. Insect Biochem Mol Biol 2004 34:305-320.
Genbank Report for Accession No. CAD57542, Direct Submission, Nov. 23, 2002.
Crickmore, Neil et al. Web <2010, http://www.lifesci.sussex.ac.uk/home/neil_Crickmore/Bt/>.

* cited by examiner

*Primary Examiner* — Sheridan Swope
(74) *Attorney, Agent, or Firm* — Alston & Bird LLP

(57) ABSTRACT

Compositions and methods for protecting a plant from an insect pest are provided. In particular, nucleic acid sequences encoding insect protoxins modified to comprise at least one proteolytic activation site that is sensitive to a plant protease or an insect gut protease are provided. Cleavage of the modified protoxin at the proteolytic activation site by a protease produces an active insect toxin. Methods of using the modified insect protoxin nucleic acid sequences and the polypeptides they encode to protect a plant from an insect pest are provided. Particular embodiments of the invention further provide modified insect protoxin compositions and formulations, expression cassettes, and transformed plants, plant cells, and seeds.

5 Claims, No Drawings

SEQUENCE LISTING

```
<160> NUMBER OF SEQ ID NOS: 7

<210> SEQ ID NO 1
<211> LENGTH: 1035
<212> TYPE: DNA
<213> ORGANISM: Diabrotica virgifera virgifera

<400> SEQUENCE: 1

gaaaaatcag aatgaagctg ttcatccttg ccgctgccct tattgtggcc acaagtgcca      60

atctaggtgc cttcgaaaaa tggaccagtt ttaaggcaac ccataacaaa tcttacaacg     120

ttattgaaga caaacttcgt ttcgctgttt tccaagacaa cctcaaaaaa atcgaggaac     180

acaatgctaa atacgaaagt ggagaagaaa cctactactt ggctgttaac aaattcgccg     240

attggtccag cgctgaattc caagctatgt tggcccgtca gatggctaac aagcccaaac     300

aatcctttat tgcaaaacac gtagccgatc ccaatgtcca agctgtagaa gaagttgatt     360

ggagagatag tgccgttttg ggagtcaaag atcaaggaca gtgtggatca tgctgggctt     420

tcagtaccac cggatccctc gaaggtcaac tcgccatcca caaaaatcaa cgtgttcctc     480

tcagtgaaca agaattggta gactgtgaca catcaagaaa tgctggttgt aacggaggtt     540

tgatgacaga tgcctttaac tatgttaaac gccatggtct ctcttccgaa tctcaatatg     600

catacaccgg cagagatgat cgctgcaaga atgttgagaa caaaccactc tcttccatta     660

gtggctacgt agaacttgaa acaactgaag atgcactcgc gtccgctgtt gctagcgtag     720

gtccagtttc catcgctgtt gatgctgata catggcaatt atacggaggt ggacttttca     780

acaacaaaaa ctgtagaacc aacctcaatc acggtgttct tgctgttgga tacactaaag     840

atgcattcat tgtcaagaac tcatggggaa ctagctgggg tgaacaaggt tacatcagag     900
```

-continued

```
ttgcccgtgg tgaaaacttg tgtggtatta acctcatgaa ctcttaccct aaattgtaaa    960

tgatttaatg caaatgaaac accaaataga attcaaaaat aaagataaat aaaaaactaa   1020

aaaaaaaaaa aaaaa                                                    1035
```

<210> SEQ ID NO 2
<211> LENGTH: 315
<212> TYPE: PRT
<213> ORGANISM: Diabrotica virgifera virgifera

<400> SEQUENCE: 2

```
Met Lys Leu Phe Ile Leu Ala Ala Ala Leu Ile Val Ala Thr Ser Ala
 1               5                  10                  15

Asn Leu Gly Ala Phe Glu Lys Trp Thr Ser Phe Lys Ala Thr His Asn
            20                  25                  30

Lys Ser Tyr Asn Val Ile Glu Asp Lys Leu Arg Phe Ala Val Phe Gln
        35                  40                  45

Asp Asn Leu Lys Lys Ile Glu Glu His Asn Ala Lys Tyr Glu Ser Gly
    50                  55                  60

Glu Glu Thr Tyr Tyr Leu Ala Val Asn Lys Phe Ala Asp Trp Ser Ser
65                  70                  75                  80

Ala Glu Phe Gln Ala Met Leu Ala Arg Gln Met Ala Asn Lys Pro Lys
                85                  90                  95

Gln Ser Phe Ile Ala Lys His Val Ala Asp Pro Asn Val Gln Ala Val
            100                 105                 110

Glu Glu Val Asp Trp Arg Asp Ser Ala Val Leu Gly Val Lys Asp Gln
        115                 120                 125

Gly Gln Cys Gly Ser Cys Trp Ala Phe Ser Thr Thr Gly Ser Leu Glu
    130                 135                 140

Gly Gln Leu Ala Ile His Lys Asn Gln Arg Val Pro Leu Ser Glu Gln
145                 150                 155                 160

Glu Leu Val Asp Cys Asp Thr Ser Arg Asn Ala Gly Cys Asn Gly Gly
                165                 170                 175

Leu Met Thr Asp Ala Phe Asn Tyr Val Lys Arg His Gly Leu Ser Ser
            180                 185                 190

Glu Ser Gln Tyr Ala Tyr Thr Gly Arg Asp Asp Arg Cys Lys Asn Val
        195                 200                 205

Glu Asn Lys Pro Leu Ser Ser Ile Ser Gly Tyr Val Glu Leu Glu Thr
    210                 215                 220

Thr Glu Asp Ala Leu Ala Ser Ala Val Ala Ser Val Gly Pro Val Ser
225                 230                 235                 240

Ile Ala Val Asp Ala Asp Thr Trp Gln Leu Tyr Gly Gly Gly Leu Phe
                245                 250                 255

Asn Asn Lys Asn Cys Arg Thr Asn Leu Asn His Gly Val Leu Ala Val
            260                 265                 270

Gly Tyr Thr Lys Asp Ala Phe Ile Val Lys Asn Ser Trp Gly Thr Ser
        275                 280                 285

Trp Gly Glu Gln Gly Tyr Ile Arg Val Ala Arg Gly Glu Asn Leu Cys
    290                 295                 300

Gly Ile Asn Leu Met Asn Ser Tyr Pro Lys Leu
305                 310                 315
```

<210> SEQ ID NO 3
<211> LENGTH: 1034
<212> TYPE: DNA
<213> ORGANISM: Diabrotica virgifera virgifera

<400> SEQUENCE: 3

```
ttttagtgag agaaaactca aaatgaagct gttaattcta gccgccaccc tcattgtggc      60
cataaatgcc aatttatctg cctttgagca atggaccagt tttaaggcaa cacacaacaa     120
attttacaac gttattgagg acaaacttcg ttttgctgtt ttccaagaga atctccgcaa     180
aatcgacgca cacaatgcta aatacgaaaa gggagaagaa acctactaca tggctgttaa     240
caaattcgcc gattggtcca gcgcagaatt ccaagccatg ttggaccgtc agatggctaa     300
caagccaaaa caatccttca ttgcaaaaca cgtagtcgat cccaatgtcc aagctgtaga     360
agaagttgat tggagagaaa gtgctgtttt gggagtcaaa gatcaaggac agtgtggatc     420
atgctgggct ttcagtacca ccggatccct cgaaggtcaa ctcgccatcc acaaaaatca     480
acgtgttcct ctcagtgaac aagaattggt agactgtgat aaggtaaacg atggttgtga     540
cggaggtttg atgacagatg ccttctttta tattgaacat catggtcttt catcagaaga     600
acaataccccc tatacaggcg tagatggtca ttgcaatcat gtaaaagaca aacaagtctc    660
ttcgatcagt ggttacgtcg aacttgatga aactgaaagt gctctagctg atgctctcgc     720
taatgttggt ccagtgtcaa tagctgtcga agctgataca tggcaattct attcaggtgg     780
agttttcaac aataaaaatt gtggagacgc tcttaaccac ggtgttcttg ctgtgggata     840
cactaaagat gtcttcatcg ttaaaaactc atggggaaca ggctggggtg aacaaggtta     900
catcagagtt gcccgtggta gcaacttatg tggtattaac ctcatgaact cttaccccaa     960
gttgtagata acagttaatg aaaagtgata tatttataat aataaatgat ataaattaca    1020
aaaaaaaaaa aaaa                                                      1034
```

<210> SEQ ID NO 4
<211> LENGTH: 314
<212> TYPE: PRT
<213> ORGANISM: Diabrotica virgifera virgifera

<400> SEQUENCE: 4

```
Met Lys Leu Leu Ile Leu Ala Ala Thr Leu Ile Val Ala Ile Asn Ala
 1               5                  10                  15

Asn Leu Ser Ala Phe Glu Gln Trp Thr Ser Phe Lys Ala Thr His Asn
            20                  25                  30

Lys Phe Tyr Asn Val Ile Glu Asp Lys Leu Arg Phe Ala Val Phe Gln
        35                  40                  45

Glu Asn Leu Arg Lys Ile Asp Ala His Asn Ala Lys Tyr Glu Lys Gly
    50                  55                  60

Glu Glu Thr Tyr Tyr Met Ala Val Asn Lys Phe Ala Asp Trp Ser Ser
65                  70                  75                  80

Ala Glu Phe Gln Ala Met Leu Asp Arg Gln Met Ala Asn Lys Pro Lys
                85                  90                  95

Gln Ser Phe Ile Ala Lys His Val Val Asp Pro Asn Val Gln Ala Val
            100                 105                 110

Glu Glu Val Asp Trp Arg Glu Ser Ala Val Leu Gly Val Lys Asp Gln
        115                 120                 125

Gly Gln Cys Gly Ser Cys Trp Ala Phe Ser Thr Thr Gly Ser Leu Glu
    130                 135                 140

Gly Gln Leu Ala Ile His Lys Asn Gln Arg Val Pro Leu Ser Glu Gln
145                 150                 155                 160

Glu Leu Val Asp Cys Asp Lys Val Asn Asp Gly Cys Asp Gly Gly Leu
                165                 170                 175
```

-continued

```
Met Thr Asp Ala Phe Phe Tyr Ile Glu His His Gly Leu Ser Ser Glu
            180                 185                 190

Glu Gln Tyr Pro Tyr Thr Gly Val Asp Gly His Cys Asn His Val Lys
        195                 200                 205

Asp Lys Gln Val Ser Ser Ile Ser Gly Tyr Val Glu Leu Asp Glu Thr
    210                 215                 220

Glu Ser Ala Leu Ala Asp Ala Leu Ala Asn Val Gly Pro Val Ser Ile
225                 230                 235                 240

Ala Val Glu Ala Asp Thr Trp Gln Phe Tyr Ser Gly Gly Val Phe Asn
                245                 250                 255

Asn Lys Asn Cys Gly Asp Ala Leu Asn His Gly Val Leu Ala Val Gly
            260                 265                 270

Tyr Thr Lys Asp Val Phe Ile Val Lys Asn Ser Trp Gly Thr Gly Trp
        275                 280                 285

Gly Glu Gln Gly Tyr Ile Arg Val Ala Arg Gly Ser Asn Leu Cys Gly
    290                 295                 300

Ile Asn Leu Met Asn Ser Tyr Pro Lys Leu
305                 310
```

<210> SEQ ID NO 5
<211> LENGTH: 3621
<212> TYPE: DNA
<213> ORGANISM: Bacillus thuringiensis

<400> SEQUENCE: 5

```
atgagtccaa ataatcaaaa tgaatatgaa attatagatg cgacaccttc tacttctgta     60

tccaatgatt ctaacagata cccttttgcg aatgagccaa caaatgcgct acaaaatatg    120

gattataaag attatttaaa aatgtctgcg ggaaatgcta gtgaataccc tggttcacct    180

gaagtacttg ttagcggaca agatgcagct aaggccgcaa ttgatatagt aggtaaatta    240

ctatcaggtt taggggtccc atttgttggg ccgatagtga gtctttatac tcaacttatt    300

gatattctgt ggccttcagg ggaaaagagt caatgggaaa tttttatgga acaagtagaa    360

gaactcatta atcaaaaaat agcagaatat gcaaggaata aagcgctttc ggaattagaa    420

ggattaggta ataattacca attatatcta actgcgcttg aagaatggga agaaaatcca    480

aatggttcaa gagccttacg agatgtgcga aatcgatttg aaatcctgga tagtttattt    540

acgcaatata tgccatcttt tagagtgaca aattttgaag taccattcct tactgtatat    600

gcaatggcag ccaaccttca tttactgtta ttaaaggacg cgtcaatttt tggagaagaa    660

tggggatggt caacaactac tattaataac tattatgatc gtcaaatgaa acttactgca    720

gaatattctg atcactgtgt aaagtggtat gaaactggtt tagcaaaatt aaaaggcacg    780

agcgctaaac aatgggttga ctataaccaa ttccgtagag aaatgacact ggcggtttta    840

gatgttgttg cattattccc aaattatgac acacgcacgt acccaatgga aacgaaagca    900

caactaacaa gggaagtata tacagatcca ctgggcgcgg taaacgtgtc ttcaattggt    960

tcctggtatg acaaagcacc ttctttcgga gtgatagaat catccgttat tcgaccaccc   1020

catgtatttg attatataac gggactcaca gtgtatacac aatcaagaag catttcttcc   1080

gctcgctata taagacattg ggctggtcat caaataagct accatcgtgt cagtaggggt   1140

agtaatcttc aacaaatgta tggaactaat caaaatctac acagcactag tacctttgat   1200

tttacgaatt atgatattta caagactcta tcaaaggatg cagtactcct tgatattgtt   1260

taccctggtt atacgtatat attttttgga atgccagaag tcgagttttt catggtaaac   1320

caattgaata ataccagaaa gacgttaaag tataatccag tttccaaaga tattatagcg   1380
```

-continued

```
agtacaagag attcggaatt agaattacct ccagaaactt cagatcaacc aaattatgag   1440
tcatatagcc atagattatg tcatatcaca agtattcccg cgacgggtaa cactaccgga   1500
ttagtacctg tattttcttg gacacatcga agtgcagatt taaacaatac aatatattca   1560
gataaaatca ctcaaattcc ggccgttaaa tgttgggata atttaccgtt tgttccagtg   1620
gtaaaaggac caggacatac aggaggggat ttattacagt ataatagaag tactggttct   1680
gtaggaacct tatttctagc tcgatatggc ctagcattag aaaaagcagg gaaatatcgt   1740
gtaagactga gatatgctac tgatgcagat attgtattgc atgtaaacga tgctcagatt   1800
cagatgccaa aaacaatgaa cccaggtgag gatctgacat ctaaaacttt taaagttgca   1860
gatgctatca caacattaaa tttagcaaca gatagttcgc tagcattgaa acataattta   1920
ggtgaagacc ctaattcaac attatctggt atagtttacg ttgaccgaat cgaattcatc   1980
ccagtagatg agacatatga agcggaacaa gatttagaag cagcgaagaa agcagtgaat   2040
gccttgttta cgaatacaaa agatggctta cgaccaggcg taacggatta tgaagtgaat   2100
caagcggcaa acttagtgga atgcctatcg gatgatttgt atccaaatga aaaacgattg   2160
ttatttgatg cagtgagaga ggcaaaacgc ctcagtgagg cacgtaattt gcttcaagat   2220
ccagatttcc aagagataaa tggagaaaat ggctggacgg caagtacggg aattgaggtt   2280
atagaagggg atgctttatt caaagggcgt tatctacgcc taccaggtgc gagagaaata   2340
gatacggaaa cgtatccaac gtatctgtat caaaaagtag aggaaggtgt attaaaacca   2400
tacacaagat atagattgag agggtttgtc ggaagcagtc aaggattgga aattttcaca   2460
attcgtcatc aaacgaaccg aattgtaaaa aatgtaccgg atgatttgct gccagatgta   2520
tctcctgtta actcggatgg tagtatcaat cgatgcagcg aacaaaagta tgtgaatagc   2580
cgtttagaag tagaaaaccg ttctggtgaa gcgcatgagt tctctattcc tattgataca   2640
ggtgaaatcg attacaatga aaatgcagga atatgggttg gatttaagat tacggaccca   2700
gagggatatg caacactcgg aaacctagaa ttggtcgaag agggaccttt atcaggagac   2760
gcattagaac gcttgcaaag agaagaacaa cagtggaaga ttcaaatgac aagaagacgt   2820
gaagaaacag atagaaggta tatggcatcg aaacaagcgg tagatcgttt atatgccgat   2880
tatcaggatc agcaactgaa tcctgatgta gagattacag atcttactgc ggcccaagat   2940
ctgatacagt ccattcctta cgtatataac gaaatgttcc cagaaatacc agggatgaac   3000
tatacgaagt ttacagaatt aacagatcga ctccaacaag cgtggagttt gtatgatcag   3060
cgaaatgcca taccaaatgg tgattttcga aatgggttaa gtaattggaa tgcaacgcct   3120
ggcgtagaag tacaacaaat caatcataca tctgtccttg tgattccaaa ctgggatgag   3180
caagtttcgc aacagtttac agttcaaccg aatcaaagat atgtgttacg agttactgcg   3240
agaaaagaag ggtaggaaa tggatatgta agtatccgtg atggtggaaa tcaaacagaa   3300
acgcttactt ttagtgcaag cgattatgat acaaatggaa tgtataatac gcaagtgtcc   3360
aatacaaatg gatataacac aaataatgcg tataatacac aagcatcgag tacaaacgga   3420
tataacgcaa ataatatgta taatacgcaa gcatcgaata caaacggata taacacaaat   3480
agtgtgtaca atgatcaaac cggctatatc acaaaaacag tgacattcat cccgtataca   3540
gatcaaatgt ggattgagat gagtgagaca gaaggtacat tctatataga aagtgtagaa   3600
ttgattgtag acgtagagta a                                              3621
```

<210> SEQ ID NO 6
<211> LENGTH: 8

-continued

```
<212> TYPE: PRT
<213> ORGANISM: Artificial Sequence
<220> FEATURE:
<223> OTHER INFORMATION: Proteolytic site

<400> SEQUENCE: 6

Phe Arg Arg Gly Phe Arg Arg Gly
1               5


<210> SEQ ID NO 7
<211> LENGTH: 4
<212> TYPE: PRT
<213> ORGANISM: Artificial Sequence
<220> FEATURE:
<223> OTHER INFORMATION: Proteolytic site

<400> SEQUENCE: 7

Asn Gly Ser Arg
1
```

NUCLEIC ACID MOLECULES ENCODNG A CATHEPSIN L-LIKE CYSTEINE PROTEASE

CROSS REFERENCE TO RELATED APPLICATIONS

This application is a divisional application of U.S. Utility application Ser. No. 11/949,912, filed Dec. 4, 2007, now U.S. Pat. No. 7,629,449, which is a divisional application of U.S. Utility application Ser. No. 11/021,115, filed Dec. 22, 2004, now U.S. Pat. No. 7,339,092, which claims priority to U.S. Provisional Application No. 60/532,185 filed on Dec. 23, 2003, all of which are herein incorporated by reference in their entirety.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 376981 SequenceListing.txt, a creation date of Jul. 20, 2009, and a size of 13 KB. The sequence listing filed via EFS-Web is part of the specification and is hereby incorporated in its entirety by reference herein.

FIELD OF THE INVENTION

The present invention relates to the fields of plant molecular biology and plant pest control. More specifically, the present invention relates to modified insect protoxins and the nucleic acid sequences that encode them. Methods of the invention utilize these modified insect protoxins and nucleic acid sequences to control plant pests.

BACKGROUND OF THE INVENTION

Insect pests are a major factor in the loss of the world's agricultural crops. For example, corn rootworm feeding damage or boll weevil damage can be economically devastating to agricultural producers. Insect pest-related crop loss from corn rootworm alone has reached one billion dollars a year.

Traditionally, the primary methods for impacting insect pest populations, such as corn rootworm populations, are crop rotation and the application of broad-spectrum synthetic chemical pesticides. However, consumers and government regulators alike are becoming increasingly concerned with the environmental hazards associated with the production and use of synthetic chemical pesticides. Because of such concerns, regulators have banned or limited the use of some of the more hazardous pesticides. Thus, there is substantial interest in developing alternatives to traditional chemical pesticides that present a lower risk of pollution and environmental hazards and provide a greater target specificity than is characteristic of traditional broad-spectrum chemical insecticides.

Certain species of microorganisms of the genus *Bacillus* are known to possess pesticidal activity against a broad range of insect pests including Lepidoptera, Diptera, Coleoptera, Hemiptera, and others. *Bacillus thuringiensis* and *Bacillus papilliae* are among the most successful biocontrol agents discovered to date. Insect pathogenicity has been attributed to strains of: *B. larvae, B. lentimorbus, B. papilliae, B. sphaericus, B. thuringiensis* (Harwook, ed. (1989) *Bacillus* (Plenum Press), p. 306) and *B. cereus* (International Publication No. WO 96/10083). Pesticidal activity appears to be concentrated in parasporal crystalline protein inclusions, although pesticidal proteins have also been isolated from the vegetative growth stage of *Bacillus*. Several genes encoding these pesticidal proteins have been isolated and characterized (see, for example, U.S. Pat. Nos. 5,366,892 and 5,840,868).

Microbial pesticides, particularly those obtained from *Bacillus* strains, have played an important role in agriculture as alternatives to chemical pest control. Pesticidal proteins isolated from strains of *Bacillus thuringiensis*, known as δ-endotoxins or Cry toxins, are initially produced in an inactive protoxin form. These protoxins are proteolytically converted into an active toxin through the action of proteases in the insect gut. See, Rukmini et al. (2000) *Biochimie* 82:109-116; Oppert (1999) *Arch. Insect Biochem. Phys.* 42:1-12 and Carroll et al. (1997) *J. Invertebrate Pathology* 70:41-49. Proteolytic activation of the toxin can include the removal of the N- and C-terminal peptides from the protein, as well as internal cleavage of the protein. Other proteases can degrade pesticidal proteins. See Oppert, ibid.; see also U.S. Pat. Nos. 6,057,491 and 6,339,491. Once activated, the Cry toxin binds with high affinity to receptors on epithelial cells in the insect gut, thereby creating leakage channels in the cell membrane, lysis of the insect gut, and subsequent insect death through starvation and septicemia. See, e.g., Li et al. (1991) *Nature* 353:815-821.

Recently, agricultural scientists have developed crop plants with enhanced insect resistance by genetically engineering crop plants to produce pesticidal proteins from *Bacillus*. For example, corn and cotton plants genetically engineered to produce Cry toxins (see, e.g., Aronson (2002) *Cell Mol. Life. Sci.* 59(3):417-425; Schnepf et al. (1998) *Microbiol. Mol. Biol. Rev.* 62(3):775-806) are now widely used in American agriculture and have provided the farmer with an environmentally friendly alternative to traditional insect-control methods. In addition, potatoes genetically engineered to contain pesticidal Cry toxins have been sold to the American farmer. The presence of endogenous proteases in plants that can degrade and inactivate the insect toxins expressed in these transgenic plants, however, limits the usefulness of these pest-control techniques.

Researchers have determined that plants express a variety of proteases, including serine and cysteine proteases. See, e.g., Goodfellow et al. (1993) *Plant Physiol.* 101:415-419; Pechan et al. (1999) *Plant Mol. Biol.* 40:111-119; Lid et al. (2002) *Proc. Nat. Acad. Sci. USA* 99:5460-5465. Previous research has also shown that insect gut proteases include cathepsins, such as cathepsin B- and L-like proteinases. See, Shiba et al. (2001) *Arch. Biochem. Biophys.* 390:28-34; Purcell et al. (1992) *Insect Biochem. Mol. Biol.* 22:41-47. For example, cathepsin L-like digestive cysteine proteinases are found in the larval midgut of Western corn rootworm. See, Koiwa et al. (2000) *FEBS Letters* 471:67-70; Koiwa et al. (2000) *Analytical Biochemistry* 282:153-155.

While investigators have previously genetically engineered plants, particularly crop plants, to contain biologically active (i.e., pesticidal) Cry toxins, these foreign proteins can be degraded and inactivated by proteases present in these transgenic plants. Moreover, researchers to date have not effectively utilized the protoxin forms of pesticidal polypeptides in conjunction with endogenous plant or insect gut proteases to control plant pests. Thus, new strategies for modifying insect toxins and utilizing these modified insect toxins in pest management strategies are desired.

BRIEF SUMMARY OF THE INVENTION

Compositions and methods for protecting a plant from an insect pest are provided. Compositions are novel nucleic acid molecules comprising nucleotide sequences encoding insect protoxins that comprise at least one proteolytic activation site that has been engineered to comprise a cleavage site that is sensitive to cleavage by a plant protease or is sensitive to cleavage by an insect gut protease. The proteolytic activation site is engineered within the activation region of the insect protoxin such that proteolytic cleavage by the plant protease or insect gut protease releases the activated insect toxin within a plant cell or within the insect gut, respectively. The novel nucleic acid molecules can be operably linked to any promoter of interest to drive expression of these modified insect protoxins in plant cells. Expression cassettes and transgenic plant cells, plants, and seeds comprising these novel nucleic acid molecules are also provided. Modified insect protoxins and methods for their use in controlling plant pests are further provided.

The nucleic acid compositions of the invention are useful in methods directed to protecting plants from insect pests and in methods for impacting insect pests. The methods comprise introducing into a plant a polynucleotide construct comprising a nucleotide sequence that encodes a modified insect protoxin operably linked to a promoter that drives expression in a plant cell. Where the modified insect protoxin comprises a proteolytic activation site that is engineered to comprise a cleavage site that is sensitive to a plant protease, expression of the polynucleotide construct produces the modified insect protoxin in the plant cell, wherein it is cleaved by a plant protease to generate the active insect toxin. The presence of the insect toxin protects the plant from an insect pest. Where the modified insect protoxin comprises a proteolytic activation site that is engineered to comprise a cleavage site that is sensitive to an insect gut protease, expression of the polynucleotide construct produces the modified insect protoxin within the cells of the transgenic plant. When a susceptible insect pest feeds on the transgenic plant and, thus, also ingests the modified protoxin that has been expressed in the plant, the modified insect protoxin is cleaved by an insect gut protease to generate the active toxin in the insect gut, thereby impacting the insect pest.

The present invention further provides nucleic acid molecules encoding novel insect gut proteases and biologically active variants and fragments thereof. The novel proteases are useful in methods directed to identification of preferred proteolytic cleavage sites for these insect gut proteases. Having identified these preferred proteolytic cleavage sites, insect protoxins of interest can be modified to comprise the preferred proteolytic cleavage sites within at least one proteolytic activation site to improve activation of the insect protoxin within an insect gut. Where an insect protoxin of interest alternatively or also comprises one or more of these preferred cleavage sites in a region of the protoxin that is outside an activation region but within the activated insect toxin, the preferred cleavage site can be replaced with a proteolytic protection site to protect the insect toxin from proteolytic inactivation in the insect gut.

DETAILED DESCRIPTION OF THE INVENTION

The present invention is directed to compositions and methods that provide for protection of a plant from insect pests, and which can be utilized to impact these insect pests. The compositions are novel nucleic acid molecules comprising nucleotide sequences encoding modified insect protoxins that provide for efficient processing into active toxins either within the cells of a plant host that is capable of expressing the modified insect protoxin or within the gut of the insect pest that feeds on a plant host that is capable of expressing the modified insect protoxin.

"Modified insect protoxin" is intended to mean an insect protoxin that comprises at least one proteolytic activation site that is not naturally occurring within the insect protoxin, and which has been engineered to comprise a cleavage site that either is sensitive to cleavage by a plant protease residing within the cells of a plant, or is sensitive to cleavage by an insect gut protease. "Sensitive to cleavage" is intended to mean that the protease recognizes the cleavage site, and thus is capable of cleaving the protoxin at that cleavage site. In both instances, the non-naturally occurring proteolytic activation site is engineered within an activation region of the insect protoxin. "Activation region" is intended to mean a region within the insect protoxin wherein proteolytic cleavage at the engineered activation site results in the production of a biologically active insect toxin. For purposes of the present invention, this biologically active insect toxin is also referred to as the "active insect toxin," the "activated insect toxin," or the "activated form" of an insect protoxin.

The compositions of the invention also include polynucleotide constructs comprising these nucleic acid molecules. These constructs include, but are not limited to, expression cassettes, wherein the nucleotide sequences encoding the modified insect protoxins are operably linked to a promoter that drives expression in a plant cell. The invention further provides plant cells, plants, and seeds stably transformed with these polynucleotide constructs. The compositions of the invention are useful in protecting a plant from insect pests, and can be utilized to impact insect pests that interact with a plant during one or more phases of the insect life cycle.

In one embodiment, the novel nucleic acid molecules of the invention comprise nucleotide sequences that encode a modified insect protoxin that comprises at least one proteolytic activation site that has been engineered to comprise a cleavage site that is sensitive to cleavage by a plant protease as noted herein below. Such nucleic acid molecules can be utilized in the methods of the invention to protect a plant from insect pests. In this manner, a polynucleotide construct comprising this type of modified insect protoxin coding sequence, operably linked to a promoter that drives expression in a plant cell, can be introduced into a plant. Expression of this polynucleotide construct within cells of this plant produces the modified insect protoxin in those cells. The inactive modified insect protoxin is then cleaved by a plant protease at the engineered proteolytic activation site to produce a biologically active insect toxin that protects the plant from an insect pest that feeds on cells of the plant comprising the active insect toxin.

In another embodiment, the novel nucleic acid molecules of the invention comprise nucleotide sequences encoding a modified insect protoxin that comprises at least one proteolytic activation site that has been engineered to comprise a cleavage site that is sensitive to cleavage by a protease that resides within an insect gut. In some embodiments, the proteolytic activation site is engineered to comprise a cleavage site that is the preferred cleavage site for a novel insect gut protease disclosed herein below. Such nucleic acid molecules can be utilized in the methods of the invention to impact insect pests. "Impact an insect pest" or "impacting an insect pest" is intended to mean, for example, deterring the insect pest from feeding further on the plant, harming the insect pest, or killing the insect pest as noted herein below. In this manner, a polynucleotide construct comprising this type of modified insect protoxin coding sequence, operably linked to a promoter that drives expression in a plant cell, can be introduced into a plant. Expression of this polynucleotide construct within cells of this plant produces the modified protoxin in those plant cells. When an insect pest feeds on cells of the plant that are expressing this modified insect protoxin, the ingested modified insect protoxin is cleaved by the insect gut protease, thereby producing an active insect toxin in the insect gut and impacting the insect pest. Cleavage can result in removal of the N-terminal sequence, the C-terminal sequence or both sequences. In addition to N- and C-terminal processing, part of the activation process may also involve cleavage between the alpha 3 and alpha 4 helices.

In other embodiments, the invention is drawn to the modified insect protoxins encoded by the nucleic acid molecules of the present invention and to methods for using these polypeptides. Compositions and formulations comprising a modified insect protoxin, or variant or fragment thereof, that comprises at least one, non-naturally occurring proteolytic activation site that has been engineered to comprise a cleavage site that is sensitive to cleavage by an insect gut protease, are useful in methods directed to impacting insect pests. In this manner, the invention further provides a method for impacting an insect pest of a plant comprising applying, for example, a composition or formulation comprising this type of modified insect protoxin to the environment of the insect pest. In one embodiment, the modified insect protoxin is combined with a carrier for subsequent application to the environment of the insect pest. While the invention is not bound by any theory of operation, in one embodiment, an insect pest ingests the modified insect protoxin. The modified protoxin is then cleaved by an insect gut protease to produce a biologically active toxin in the insect pest gut, thereby impacting the insect pest.

One of skill in the art would recognize that the compositions and methods of the invention can be used alone or in combination with other compositions and methods for controlling insect pests that impact plants. For example, the present invention may be used in conjunction with other pesticidal proteins or traditional chemical pesticides.

While the invention does not depend on a particular biological mechanism for protecting a plant from an insect pest, expression of the nucleotide sequences of the invention in a plant can result in the production of active insect toxins that increase the resistance of the plant to insect pests. The transgenic plants of the invention find use in agriculture in methods for protecting plants from insect pests and for impacting insect pests. Certain embodiments of the invention provide transformed crop plants, such as, for example, maize plants, which find use in methods for impacting insect pests of the plant, such as, for example, western, northern, southern, and Mexican corn rootworms. Other embodiments of the invention provide transformed potato plants, which find use in methods for impacting the Colorado potato beetle, transformed cotton plants, which find use in methods for impacting the cotton boll weevil, and transformed turf grasses, which find use in methods for impacting the bluegrass billbug, *Sphenophorous parvulus*.

"Insect protoxin" or "protoxin" is intended to mean a biologically inactive polypeptide that is converted to an active insect toxin upon cleavage at a proteolytic activation site by a protease. In some embodiments, activation of the toxin proceeds by removal of a C-terminal peptide, an N-terminal peptide, or peptides from both the N-terminal and C-terminal regions of the protoxin. "Insect toxin" refers to the activated form of an insect protoxin, i.e., the cleaved polypeptide that possesses pesticidal activity. As used herein, the term "pesticidal activity" refers to activity of a substance, such as, for example, a protein, that can be measured by routine assays known in the art. Such assays include, but are not limited to, pest mortality, pest weight loss, pest repellency, pest attraction, and other behavioral and physical changes of a pest after feeding and exposure to the substance for an appropriate length of time. General procedures include addition of the experimental compound or organism to the diet source in an enclosed container. Assays for assessing pesticidal activity are well known in the art. See, e.g., U.S. Pat. Nos. 6,570,005 and 6,339,144; herein incorporated by reference in their entirety.

The preferred developmental stage for testing for pesticidal activity is larvae or immature forms of an insect of interest. The insects may be reared in total darkness at from about 20° C. to about 30° C. and from about 30% to about 70% relative humidity. Bioassays may be performed as described in Czapla and Lang (1990) *J. Econ. Entomol.* 83(6):2480-2485. Methods of rearing insect larvae and performing bioassays are well known to one of ordinary skill in the art.

In some embodiments of the invention, the insect toxin is a *Bacillus thuringiensis* (Bt) toxin. "Bt" or "*Bacillus thuringiensis*" toxin is intended to mean the broader class of toxins found in various strains of *Bacillus thuringiensis*, which includes such toxins as, for example, the vegetative insecticidal proteins and the δ-endotoxins. The vegetative insecticidal proteins (for example, members of the VIP1, VIP2, or VIP3 classes) are secreted insecticidal proteins that undergo proteolytic processing by midgut insect fluids. They have pesticidal activity against a broad spectrum of Lepidopteran insects. See, for example, U.S. Pat. No. 5,877,012, herein incorporated by reference in its entirety. The Bt δ-endotoxins are toxic to larvae of a number of insect pests, including members of the Lepidoptera, Diptera, and Coleoptra orders. These insect protoxins include, but are not limited to, the crytoxins, including, for example, Cry 1, Cry 3, Cry 5, Cry 8, and Cry 9. Of particular interest are the Cry 8 or Cry 8-like δ-endotoxins. "Cry 8-like" is intended to mean that the nucleotide or amino acid sequence shares a high degree of sequence identity or similarity to previously described sequences categorized as Cry8, which includes such toxins as, for example, Cry8Bb1 (see Genbank Accession No. CAD57542) and Cry8Bc1 (see Genbank Accession No. CAD57543). See co-pending U.S. patent application Ser. No. 10/666,320, filed Jun. 25, 2003, herein incorporated by reference. "Cry8-like insect protoxin" is intended to mean the biologically inactive polypeptide that is converted to the activated Cry8-like insect toxin upon cleavage at a proteolytic activation site by a protease. It is the activated Cry8-like insect toxin that has pesticidal activity. As used herein, "Cry8-like insect toxin" refers to a biologically active pesticidal polypeptide that shares a high degree of sequence identity or similarity to Cry8 insect toxin sequences.

The Bt toxins are a family of insecticidal proteins that are synthesized as protoxins and crystallize as parasporal inclusions. When ingested by an insect pest, the microcrystal structure is dissolved by the alkaline pH of the insect midgut, and the protoxin is cleaved by insect gut proteases to generate the active toxin. The activated Bt toxin binds to receptors in the gut epithelium of the insect, causing membrane lesions and associated swelling and lysis of the insect gut. Insect death results from starvation and septicemia. See, e.g., Li et al. (1991) *Nature* 353:815-821.

The protoxin form of the Cry toxins contains a crystalline forming segment. A comparison of the amino acid sequences of active Cry toxins of different specificities further reveals five highly-conserved sequence blocks. Structurally, the Cry toxins comprise three distinct domains, which are, from the N- to C-terminus: a cluster of seven alpha-helices implicated in pore formation (referred to as "domain 1"), three anti-parallel beta sheets implicated in cell binding (referred to as "domain 2"), and a beta sandwich (referred to as "domain 3"). The location and properties of these domains are known to those of skill in the art. See, for example, Li et al. (1991) supra and Morse et al. (2001) *Structure* 9:409-417.

The modified insect protoxins of the invention can be derived from any suitable native (i.e., naturally occurring) insect protoxin, such as the native Bt δ-endotoxins described above, by engineering the proteolytic activation site of interest within the native insect protoxin sequence. In this manner, a nucleotide sequence encoding the native insect protoxin of interest can be altered, for example, by site-directed mutagenesis, to comprise the codons for the proteolytic activation site of interest, i.e., a site sensitive to plant proteases or a site sensitive to insect gut proteases. As noted above, the codons for the proteolytic activation site(s) of interest are engineered within the region of the native coding sequence that corresponds to the activation region of the native insect protoxin, so that proteolytic cleavage of the encoded modified insect protoxin by the protease of interest results in production of the active insect toxin.

Alternatively, the modified insect protoxins of the invention can be derived from fragments or variants of native insect protoxins, as defined herein below, so long as the fragment or variant of the native insect protoxin yields an activated (i.e., having pesticidal activity) insect toxin upon proteolytic cleavage by the protease of interest (i.e., plant protease or insect gut protease). In this manner, the coding sequences for such fragments and variants of the native insect protoxin protein serve as the starting material for engineering in the codons for the proteolytic activation site(s) of interest. In essence, a modified insect protoxin designed in this manner represents a fragment or variant of the native insect protoxin that has been engineered to comprise the proteolytic activation site of interest within the activation region of the respective polypeptide.

It is recognized that variations in a modified insect protoxin disclosed herein can be introduced at the level of the nucleic acid molecule that encodes a modified form of a native insect protoxin in order to produce a variant of the encoded modified insect protoxin. That is, having disclosed a nucleotide sequence encoding a native insect protoxin with at least one proteolytic activation site of interest engineered within the native insect protoxin sequence, one of skill in the art can subsequently introduce variations into the disclosed nucleotide sequence of the invention, so that the encoded modified insect protoxin is a variant of the modified native insect protoxin. Such variations include deletions, substitutions, and additions of one or more residues, and include variations that result in truncated forms of the modified insect protoxin. Any such variations can be introduced into the nucleotide sequence encoding the modified native insect protoxin so long as the encoded variant of the modified insect protoxin can be cleaved to produce a biologically active insect toxin, i.e., an insect toxin that has pesticidal activity as noted elsewhere herein. Such variants and fragments are well-known in the art. See, e.g., co-pending U.S. patent application Ser. No. 10/606,320, filed Jun. 25, 2003; U.S. Pat. No. 5,877,012; herein incorporated by reference in their entirety.

"Protecting a plant from an insect pest" is intended to mean limiting or eliminating insect pest-related damage to a plant by, for example, inhibiting the ability of the insect pest to grow, feed, and/or reproduce or by killing the insect pest.

As used herein, "impacting an insect pest of a plant" includes, but is not limited to, deterring the insect pest from feeding further on the plant, harming the insect pest by, for example, inhibiting the ability of the insect to grow, feed, and/or reproduce, or killing the insect pest.

A "protease" is intended to mean an enzyme that cleaves polypeptides by hydrolyzing peptide bonds. A "plant protease" is intended to mean a protease that is naturally found in any plant of the invention. Previous research has shown that plants express a variety of proteases, including serine and cysteine proteases. See, e.g., Goodfellow et al. (1993) *Plant Physiol.* 101:415-419; Pechan et al. (1999) *Plant Mol. Biol.* 40:111-119; Lid et al. (2002) *Proc. Nat. Acad. Sci. USA* 99:5460-5465. Any plant protease may be used in the present invention. In some embodiments, the plant protease is a cysteine protease, for example, a cathepsin or cathepsin-like protease. In one embodiment, the cysteine protease is a cathepsin B-like protease.

As used herein, "insect gut protease" refers to a protease that is naturally found in the digestive tract of an insect pest. Researchers have established that a wide array of proteases are expressed in the insect gut, including cysteine and serine proteases. See, e.g., Shiba et al. (2001) *Arch. Biochem. Biophys.* 390:28-34; see also, Purcell et al. (1992) *Insect Biochem. Mol. Biol.* 22:1-47; Koiwa et al. (2000) *FEBS Letters* 471:67-70; Koiwa et al. (2000) *Anal. Biochem.* 282: 153-155. Any insect gut protease may be used in the present invention. In some embodiments, the insect gut protease is a cysteine protease, for example, a cathepsin B-like or cathepsin L-like protease. In other embodiments, the insect gut protease is a serine protease, for example, trypsin or chymotrypsin.

A "proteolytic site" is intended to mean an amino acid sequence that confers sensitivity to a class of proteases or a particular protease such that a polypeptide comprising the amino acid sequence is cleaved at that site by members of the class of proteases or by the particular protease. As used herein, a "proteolytic activation site" is a proteolytic site that has been engineered into an activation region of an insect protoxin. As used herein, an "activation region" is a region of an insect protoxin such that proteolytic cleavage at the proteolytic activation site within the activation region generates a biologically active insect toxin. A proteolytic site is said to be "sensitive" to the protease(s) that recognizes that site. It is recognized that the efficiency of proteolytic digestion will vary, and that a decrease in efficiency of proteolytic digestion can lead to an increase in stability or longevity of the polypeptide within a plant cell or within an insect gut. Thus, a proteolytic site may confer sensitivity to more than one protease or class of proteases, but the efficiency of digestion at that site by various proteases may vary.

Proteolytic sites include, for example, trypsin sites, chymotrypsin sites, papain sites, cathepsin sites, and cathepsin-like sites. Proteolytic sites for particular proteases often comprise "motifs," or sequence patterns, that are known to confer sensitivity to a particular protease. Thus, for example, cathepsin site motifs include FRR, a cathepsin L protease cleavage site; RR, a trypsin and cathepsin B cleavage site; LKM, a chymotrypsin site; and FF, a cathepsin D site. A putative proteolytic site is a sequence that comprises a motif or comprises a sequence similar to a motif but which has not been shown to be subject to digestion by the corresponding protease. In one embodiment, the modified insect protoxins of the invention have a proteolytic activation site that comprises the motif FRRGFRRG (SEQ ID NO:6).

In some embodiments of the invention, the proteolytic activation site is introduced in the C-terminal portion of the protoxin, the N-terminal portion of the protoxin, or in both the N-terminal and C-terminal regions. Likewise, in some embodiments, cleavage of the protoxin will result in the removal of an N-terminal peptide, a C-terminal peptide, or peptides from both the N-terminal and C-terminal regions of the protein. In one particular embodiment, the proteolytic activation site is introduced in the junction between the N-terminal crystalline forming segment of the protoxin and the C-terminal portion of the protoxin that comprises the active insect toxin upon cleavage.

It is further recognized that insect toxins expressed in a plant cell may be susceptible to further cleavage by plant proteases. Cleavage of the active insect toxin at a naturally occurring proteolytic site may lead to proteolytic inactivation of the toxin. As used herein, "proteolytic inactivation" connotes cleavage of the active insect toxin at a naturally occurring proteolytic site by a plant protease, wherein cleavage at that site reduces or eliminates the pesticidal activity of the insect toxin. In one embodiment, the insect toxin is engineered to replace a naturally occurring proteolytic site that is sensitive to cleavage by a plant protease with a proteolytic protection site. A "proteolytic protection site" is intended to mean a site that is not sensitive to cleavage by an endogenous plant protease. Replacement of a naturally occurring proteolytic site sensitive to cleavage by a plant protease with a proteolytic protection site protects the insect toxin from proteolytic inactivation by the plant. See co-pending U.S. patent application Ser. No. 10/746,914, entitled "Genes Encoding Proteins with Pesticidal Activity," filed Dec. 23, 2003, herein incorporated by reference.

In some embodiments, an insect protoxin is engineered to comprise a proteolytic activation site that is recognized by a novel insect gut protease. The invention provides nucleic acid molecules, and variants and fragments thereof, that encode novel insect gut proteases. Specifically, the invention provides nucleic acid molecules encoding novel proteases identified in the midgut of *Diabrotica virgifera virgifera* (i.e., western corn rootworm, hereinafter WCRW). The nucleotide sequences set forth in SEQ ID NOs:1 and 3 encode novel cysteine proteases that belong to the cathepsin L-like subfamily of proteases. The nucleotide sequences set forth in SEQ ID NOs:1 and 3 encode the polypeptide sequences (i.e., proteases) of SEQ ID NOs:2 and 4, respectively. The invention further encompasses variants and fragments of these polypeptide sequences that possess proteolytic activity as defined herein below. Assays for measuring proteolytic activity are well known in the art.

Studies indicate that the novel cathepsin L-like proteases of the invention represent the two most abundant forms of the cathepsin-type proteases expressed within the WCRW midgut and, therefore, are expected to be significantly involved in the digestive process. Previous research has demonstrated that mammalian cathepsin L-like proteases have a general preference for F-R-(A/S/K/N/Q) with cleavage C-terminal to the arginine position. Little is known about the proteolytic cleavage site(s) for insect pest cathepsin L-like proteases. Thus, the novel WCRW gut proteases of the invention find use, for example, in identifying the preferred proteolytic cleavage site(s) for these proteases. In another embodiment, the insect gut proteases are used to identify proteolytic cleavage sites within pesticidal polypeptides, such as Cry8Bb1 and Cry8Bc1, that are susceptible to these proteases.

Knowledge about the preferred proteolytic sites for the insect gut proteases of the invention may lead to improvements in the activation and stability of insect toxins. For example, a proteolytic activation site that is sensitive to cleavage by an insect gut protease of the invention may be introduced into an activation region of an insect protoxin. When this modified protoxin is expressed in a plant and an insect pest, such as WCRW, feeds on the transgenic plant, the protoxin is cleaved by a cathepsin L-like protease of the invention in the insect gut, thereby producing the active toxin and impacting the insect pest. In one embodiment, the engineered proteolytic activation site is sensitive to cleavage by the cathepsin L-like protease of SEQ ID NO:2 or 4. In some embodiments, the insect protoxin is Cry8Bb1 or Cry8Bc1.

It is further recognized that insect protoxins or toxins expressed in a plant may be susceptible to cleavage by insect gut proteases upon ingestion by an insect pest. Cleavage of an active insect toxin by an insect gut protease may lead to proteolytic inactivation of the toxin. In this context, "proteolytic inactivation" refers to cleavage of an insect toxin at a proteolytic site by an insect gut protease, wherein cleavage at that site reduces or eliminates the pesticidal activity of the toxin. In one embodiment, an insect toxin is engineered to replace a proteolytic site that is sensitive to cleavage by an insect gut protease with a proteolytic protection site. By "proteolytic protection site," a site that is not sensitive to cleavage by an insect gut protease is intended. Replacement of a proteolytic site sensitive to cleavage by an insect gut protease with a proteolytic protection site protects the insect toxin from proteolytic inactivation in the insect gut. Eliminating protease-sensitive sites may prevent the insect toxin from rapid degradation in the insect midgut after ingestion, allowing the toxin to reach its target intact and more rapidly reach an insecticidal dose within the insect pest. In one embodiment, the proteolytic protection site is engineered to be insensitive to cleavage by a cathepsin L-like protease of the invention, i.e., the polypeptide of SEQ ID NO:2 or 4. In some embodiments, the insect toxin is Cry8Bb1 or Cry8Bc1.

The nucleic acids of the invention encoding the novel cathepsin L-like insect gut proteases (SEQ ID NOs:1 and 3) and the polypeptides they encode (SEQ ID NOs:2 and 4) find further use in identifying and designing inhibitors of these proteases. Chemical and biological agents that inhibit these proteases could exhibit strong pesticidal effects upon insect feeding. For example, such inhibitors may result in the inability of the insect pest to digest food and supply the necessary dietary factors needed to support growth and development. In some embodiments, the inhibitors of the novel cathepsin L-like proteases of the invention are polypeptides. In a particular embodiment, nucleic acid molecules encoding the polypeptide inhibitors of the insect gut proteases of the invention are used to generate transgenic plants. These plants find use in controlling an insect pest of a plant. In other embodiments, polypeptide inhibitors of the cathepsin L-like proteases of the invention are used to control pests by applying the inhibitor composition to the environment of pest.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

The use of the terms "polynucleotide constructs" or "nucleotide constructs" herein is not intended to limit the present invention to nucleotide constructs comprising DNA. Those of ordinary skill in the art will recognize that nucleotide constructs, particularly polynucleotides and oligonucleotides composed of ribonucleotides and combinations of ribonucleotides and deoxyribonucleotides, may also be employed in the methods disclosed herein. The nucleotide constructs, nucleic acids, and nucleotide sequences of the invention additionally encompass all complementary forms of such constructs, molecules, and sequences. Further, the nucleotide constructs, nucleotide molecules, and nucleotide sequences of the present invention encompass all nucleotide constructs, molecules, and sequences which can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the invention also encompass all forms of nucleotide constructs including, but not limited to, single-stranded forms, double-stranded forms, hairpins, stem-and-loop structures, and the like.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

As used herein, the term "recombinantly engineered" or "engineered" or "modified" connotes the utilization of recombinant DNA technology to introduce (e.g., engineer) a change in the protein structure based on an understanding of the protein's mechanism of action and a consideration of the amino acids being introduced, deleted, or substituted. For example, a nucleic acid molecule encoding an insect protoxin may be engineered to comprise a coding sequence for a proteolytic activation site as described elsewhere herein.

As used herein, "full-length sequence" in reference to a specified polynucleotide or its encoded protein means having the entire nucleic acid sequence or the entire amino acid sequence of a native sequence. "Native sequence" is intended to mean an endogenous sequence, i.e., a non-engineered sequence found in an organism's genome. A full-length polynucleotide encodes the full-length form of the specified protein.

As used herein, the term "antisense" used in the context of orientation of a nucleotide sequence refers to a duplex polynucleotide sequence that is operably linked to a promoter in an orientation where the antisense strand is transcribed. The antisense strand is sufficiently complementary to an endogenous transcription product such that translation of the endogenous transcription product is often inhibited. Thus, where the term "antisense" is used in the context of a particular nucleotide sequence, the term refers to the complementary strand of the reference transcription product.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogues of natural amino acids that can function in a similar manner as naturally occurring amino acids.

Polypeptides of the invention can be produced either from a nucleic acid disclosed herein, or by the use of standard molecular biology techniques. For example, a truncated protein of the invention can be produced by expression of a recombinant nucleic acid of the invention in an appropriate host cell, or alternatively by a combination of ex vivo procedures, such as protease digestion and purification.

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized.

An "isolated" nucleic acid is free of sequences (optimally protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

As used herein, the term "isolated" or "purified" as it is used to refer to a protein of the invention, means that the isolated protein is substantially free of cellular material, and includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed nucleotide sequences and proteins (i.e., insect protoxins and insect gut proteases) encoded thereby are also encompassed by the present invention. A "fragment" is intended to mean a portion of a nucleotide sequence of the invention or a portion of an amino acid sequence of a polypeptide of the invention. Fragments of a nucleotide sequence may encode protein fragments that retain the biological activity of the native protein. Hence, fragments of an insect protoxin nucleotide sequence may encode protein fragments that become active insect toxins (i.e., possess pesticidal activity) upon cleavage by a protease. In contrast, fragments of an insect gut protease nucleotide sequence of the invention may encode protein fragments that have proteolytic activity as described herein and recognize the preferred proteolytic cleavage site of the native protease. Alternatively, fragments of a nucleotide sequence that are useful as hybridization probes generally do not encode fragment proteins retaining biological activity as defined herein above. Thus, fragments of a nucleotide sequence may range from at least about 20 nucleotides, about 50 nucleotides, about 100 nucleotides, and up to the full-length nucleotide sequence encoding the polypeptides of the invention.

A fragment of a nucleotide sequence of the invention that encodes a biologically active portion of a protein of the invention will encode at least 15, 25, 30, 50, 100, 200, or 300 contiguous amino acids, or up to the total number of amino acids present in a full-length polypeptide of the invention. Fragments of a nucleotide sequence that are useful as hybridization probes or PCR primers generally need not encode a biologically active portion of a protein of the invention.

Thus, a fragment of a nucleotide sequence of the invention may encode a biologically active portion of a protoxin or insect gut protease, or it may be a fragment that can be used as a hybridization probe or PCR primer using methods disclosed below. For example, a biologically active portion of an insect gut protease can be prepared by isolating a portion of one of the insect gut protease nucleotide sequences of the invention, expressing the encoded portion of the protease (e.g., by recombinant expression in vitro), and assessing the proteolytic activity of the encoded portion of the insect gut protease Nucleic acid molecules that are fragments of a nucleotide sequence of the invention comprise at least 16, 20, 50, 75, 100, 150, 200, 250, 300, 350, 400, 450, 500, 550, 600, 650, 700, 800, 900, 1,000, 1,100, 1,200, 1,300, or 1,400 nucleotides, or up to the number of nucleotides present in a full-length nucleotide sequence disclosed herein "Variants" is intended to mean substantially similar sequences. For nucleotide sequences, a variant comprises a deletion and/or addition of one or more nucleotides at one or more internal sites within the native nucleotide sequence and/or a substitution of one or more nucleotides at one or more sites in the native nucleotide sequence. As used herein, a "native" nucleotide sequence or polypeptide comprises a naturally occurring nucleotide sequence or amino acid sequence, respectively. For nucleotide sequences, conservative variants include those sequences that, because of the degeneracy of the genetic code, encode the amino acid sequence of one of the polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived polynucleotides, such as those generated, for example, by using site-directed mutagenesis but which still encode am insect protoxin or insect gut protease of the invention. Generally, variants of a particular nucleotide sequence of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular nucleotide sequence as determined by sequence alignment programs and parameters described elsewhere herein.

Variants of a particular nucleotide sequence of the invention (i.e., the reference nucleotide sequence) can also be evaluated by comparison of the percent sequence identity between the polypeptide encoded by a variant nucleotide sequence and the polypeptide encoded by the reference nucleotide sequence. Thus, for example, isolated nucleic acids that encode a polypeptide with a given percent sequence identity to an insect protoxin or insect gut protease of the invention are disclosed. Percent sequence identity between any two polypeptides can be calculated using sequence alignment programs described elsewhere herein using default parameters. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

By "variant" protein, a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they continue to possess the desired biological activity of the native protein. Hence, a variant of an insect protoxin of the invention becomes an active insect toxin (i.e., possesses pesticidal activity) upon cleavage by a protease. In the case of an insect gut protease of the invention, a variant has proteolytic activity as described herein and recognizes the preferred proteolytic cleavage site of the native protease. Such variants may result from, for example, genetic polymorphism or from human manipulation. Biologically active variants of a native protein of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs described elsewhere herein using default parameters. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the proteins of the invention can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferable.

Thus, the nucleotide sequences of the invention include both the naturally occurring sequences as well as mutant forms. Likewise, the proteins of the invention encompass both naturally occurring proteins as well as variations and modified forms thereof. Such variants will continue to possess the desired biological activity. Obviously, the mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity of an insect protoxin of the invention can be evaluated by, for example, insect-feeding assays. See, e.g., Marrone et al. (1985) *J. Econ. Entomol.* 78:290-293 and Czapla and Lang (1990) supra, herein incorporated by reference. Assays for assessing the proteolytic activity of an insect gut protease of the invention are well known in the art.

Variant nucleotide sequences also encompass sequences and proteins derived from a mutagenic and recombinogenic procedure such as DNA shuffling. With such a procedure, one or more different coding sequences can be manipulated to create a new protein possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the invention can be used to isolate corresponding sequences from other organisms, particularly other insects. In this manner, methods such as PCR, hybridization, and the like can be used to identify such sequences based on their sequence homology to the insect gut protease sequences set forth herein. Sequences isolated based on their sequence identity to an entire insect gut protease sequence set forth herein or to fragments thereof are encompassed by the present invention. Such sequences include sequences that are orthologs of the disclosed sequences. By "orthologs," genes derived from a common ancestral gene and which are found in different species as a result of speciation are intended. Genes found in different species are considered orthologs when their nucleotide sequences and/or their encoded protein sequences share substantial identity as defined elsewhere herein. Functions of orthologs are often highly conserved among species. Thus, isolated sequences that encode an insect gut protease and which hybridize under stringent conditions to an insect gut protease sequence disclosed herein, or to fragments thereof, are encompassed by the present invention.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.), hereinafter "Sambrook." See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the insect gut protease sequences of the invention. Methods for preparation of probes for hybridization and for construction of cDNA and genomic libraries are generally known in the art and are disclosed in Sambrook.

For example, an entire insect gut protease sequence disclosed herein, or one or more portions thereof, may be used as a probe capable of specifically hybridizing to corresponding insect gut protease sequences and messenger RNAs. To achieve specific hybridization under a variety of conditions, such probes include sequences that are unique among insect gut protease sequences of the invention and are at least about 10 nucleotides in length or at least about 20 nucleotides in length. Such probes may be used to amplify corresponding insect gut protease sequences from a chosen organism, i.e., an insect pest, by PCR. This technique may be used to isolate additional coding sequences from a desired insect pest or as a diagnostic assay to determine the presence of coding sequences in an insect pest. Hybridization techniques include hybridization screening of plated DNA libraries (either plaques or colonies; see, for example, Sambrook.

Hybridization of such sequences may be carried out under stringent conditions. "Stringent conditions" or "stringent hybridization conditions" is intended to mean conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length or less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C. for at least 4 hours, more optimally up to 12 hours or longer, and a final wash in 0.1×SSC at 60 to 65° C. for at least about 20 minutes. Optionally, wash buffers may comprise about 0.1% to about 1% SDS. Duration of hybridization is generally less than about 24 hours, usually about 4 to about 12 hours. The duration of the wash time will be at least a length sufficient to reach equilibrium.

Specificity is typically the function of post-hybridization washes, the critical factors being the ionic strength and temperature of the final wash solution. For DNA-DNA hybrids, the $T_m$ (thermal melting point) can be approximated from the equation of Meinkoth and Wahl (1984) *Anal. Biochem.* 138: 267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook. Thus, for example, isolated sequences that encode an insect gut protease of the invention and which hybridize under stringent conditions to insect gut protease sequences disclosed herein, or to fragments thereof, are encompassed by the present invention.

The following terms are used to describe the sequence relationships between two or more nucleic acids or polynucleotides: (a) “reference sequence,” (b) “comparison window,” (c) “sequence identity,” (d) “percentage of sequence identity,” and (e) “substantial identity.”

(a) As used herein, “reference sequence” is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, “comparison window” makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. “Equivalent program” is intended to mean any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2,3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 80%, 90%, or 95% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, 70%, 80%, 90%, and 95%.

Another indication that nucleotide sequences are substantially identical is if two molecules hybridize to each other under stringent conditions. Generally, stringent conditions are selected to be about 5° C. lower than the $T_m$ for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 80%, 85%, 90%, or 95% sequence identity to the reference sequence over a specified comparison window. Optimal alignment is conducted using the homology alignment algorithm of Needleman and Wunsch (1970) supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The modified insect protoxin nucleotide sequences of the invention are provided in expression cassettes for expression in the plant of interest. The cassette will include 5' and 3' regulatory sequences operably linked to a nucleotide sequence of the invention. "Operably linked" is intended to mean a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the protoxin nucleotide sequence to be under the transcriptional regulation of the regulatory regions. The expression cassette may additionally contain selectable marker genes.

The expression cassette will include in the 5'-3' direction of transcription, a transcriptional and translational initiation region (i.e., a promoter), a modified insect protoxin coding sequence of the invention, and a transcriptional and translational termination region (i.e., termination region) functional in plants. The promoter may be native or analogous, or foreign or heterologous, to the plant host and/or to the native insect protoxin nucleotide sequence that is engineered to encode a modified insect protoxin of the invention. Additionally, the promoter may be the natural sequence or alternatively a synthetic sequence. Where the promoter is "foreign"

or "heterologous" to the plant host, it is intended that the promoter is not found in the native plant into which the promoter is introduced. Where the promoter is "foreign" or "heterologous" to the native insect protoxin nucleotide sequence, it is intended that the promoter is not the native or naturally occurring promoter for the operably linked native insect protoxin nucleotide sequence that has been engineered to encode a modified insect protoxin of the invention. As used herein, a chimeric gene comprises a coding sequence operably linked to a transcription initiation region that is heterologous to the coding sequence.

The termination region may be native with the transcriptional initiation region, may be native with the operably linked native protoxin nucleotide sequence that has been engineered, may be native with the plant host, or may be derived from another source (i.e., foreign or heterologous to the promoter, the native protoxin sequence that has been engineered, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the nucleic acid molecules of the invention may be optimized for increased expression in the transformed plant. That is, a sequence can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al (1987) *Cell* 49:603-612; Figge et al. (1988) *Cell* 52:713-722; Deuschle et al (1989) *Proc. Natl. Acad. Sci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al (1993) *Proc. Natl. Acad. Sci. USA* 90:1917-1921; Labow et al (1990) *Mol. Cell. Biol.* 10:3343-3356; Zambretti et al. (1992) *Proc. Natl. Acad. Sci. USA* 89:3952-3956; Baim et al (1991) *Proc. Natl. Acad. Sci. USA* 88:5072-5076; Wyborski et al (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al (1988) *Biochemistry* 27:1094-1104; Bonin (1993) Ph.D. Thesis, University of Heidelberg; Gossen et al (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724; and U.S. application Ser. Nos. 10/004,357; and 10/427,692. Such disclosures are herein incorporated by reference.

The above list of selectable marker genes is not meant to be limiting. Any selectable marker gene can be used in the present invention.

A number of promoters can be used in the practice of the invention. The promoters can be selected based on the desired outcome. That is, the nucleic acids can be combined with constitutive, tissue-preferred, or other promoters for expression in plants. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611.

Generally, it will be beneficial to express the modified insect protoxin sequences from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant. Path.* 41:189-200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2): 141-150); and the like, herein incorporated by reference.

Chemical-regulated promoters can be used to modulate the expression of a modified insect protoxin sequence in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced modified insect protoxin expression within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *PlantJ.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10): 1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1): 1'-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10: 108, herein incorporated by reference. Such seed-preferred promoters include, but are not limited to, Cim1 (cytokinin-induced message); cZ19B1 (maize 19 kDa zein); and milps (myo-inositol-1-phosphate synthase); (see WO 00/11177 and U.S. Pat. No. 6,225,529, herein incorporated by reference).

Gamma-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference. A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, a "weak promoter" is intended to mean a promoter that drives expression of a coding sequence at a low level. By low level expression, levels of about 1/1000 transcripts to about 1/100,000 transcripts to about 1/500,000 transcripts is intended. Alternatively, it is recognized that weak promoters also encompasses promoters that are expressed in only a few cells and not in others to give a total low level of expression. Where a promoter is expressed at unacceptably high levels, portions of the promoter sequence can be deleted or modified to decrease expression levels.

Such weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

The methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lecl transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783 and 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (*London*) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the insect protoxin or insect gut protease sequences of the invention can be provided to a plant using a variety of transient transformation methods. Such transient transformation methods include, but are not limited to, the introduction of the insect protoxin or insect gut protease protein or variants and fragments thereof directly into the plant or the introduction of the a protein transcript into the plant. Such methods include, for example, microinjection or particle bombardment. See, for example, Crossway et al. (1986) *Mol. Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the insect protoxin or insect gut protease polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which its released to become integrated into the genome is greatly reduced. Such methods include the use particles coated with polyethylimine (PEI; Sigma #P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. It is recognized that the an insect protoxin or insect gut protease of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

The invention also encompasses transformed or transgenic plants comprising at least one nucleotide sequence of the invention. Optimally, the plant is stably transformed with a nucleotide construct comprising at least one nucleotide sequence of the invention operably linked to a promoter that drives expression in a plant cell. As used herein, the terms "transformed plant" and "transgenic plant" refer to a plant that comprises within its genome a heterologous polynucleotide. Generally, the heterologous polynucleotide is stably integrated within the genome of a transgenic or transformed plant such that the polynucleotide is passed on to successive generations. The heterologous polynucleotide may be integrated into the genome alone or as part of a recombinant expression cassette.

It is to be understood that as used herein the term "transgenic" includes any cell, cell line, callus, tissue, plant part, or plant the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, the term "plant" includes reference to whole plants, plant organs (e.g., leaves, stems, roots, etc.), seeds, plant cells, and progeny of same. Parts of transgenic plants are to be understood within the scope of the invention to comprise, for example, plant cells, protoplasts, tissues, callus, embryos as well as flowers, ovules, stems, fruits, leaves, roots originating in transgenic plants or their progeny previously transformed with a DNA molecule of the invention and therefore consisting at least in part of transgenic cells, are also an object of the present invention.

As used herein, the term "plant cell" includes, without limitation, seeds, suspension cultures, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants. Such plants include, for example, *Solanum tuberosum* and *Zea mays.*

The present invention may be used for transformation and protection of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), *macadamia* (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.), more optimally corn and soybean plants, yet more optimally corn plants.

Plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

In the present invention, an isolated modified insect protoxin protein can be formulated with an acceptable carrier into a protoxin composition or formulation that is, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area, plant, or seed to be treated. For example, the compositions of the present invention may be applied to grain in preparation for or during storage in a grain bin or silo, etc. The compositions of the present invention may be applied simultaneously or in succession with other compounds. Methods of applying an active ingredient of the present invention or an agrochemical composition of the present invention that contains at least one of the modified protoxin proteins of the present invention include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkylbenzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The compositions of the present invention can be in a suitable form for direct application or as a concentrate of primary composition that requires dilution with a suitable quantity of water or other diluant before application. The modified insect protoxin concentration will vary depending upon the nature of the particular formulation, specifically, whether it is a concentrate or to be used directly. The composition contains 1 to 98% of a solid or liquid inert carrier, and 0 to 50%, optimally 0.1 to 50% of a surfactant. These compositions will be administered at the labeled rate for the commercial product, optimally about 0.01lb-5.0 lb. per acre when in dry form and at about 0.01 pts.-10 pts. per acre when in liquid form.

In a further embodiment, the compositions of the invention can be treated prior to formulation to prolong the pesticidal activity when applied to the environment of a target pest as long as the pretreatment is not deleterious to the activity. Such treatment can be by chemical and/or physical means as long as the treatment does not deleteriously affect the properties of the composition(s). Examples of chemical reagents include but are not limited to halogenating agents; aldehydes such a formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W.H. Freeman and Co.).

The protoxin compositions and formulations of the invention can be applied to the environment of an insect pest by, for example, spraying, atomizing, dusting, scattering, coating or pouring, introducing into or on the soil, introducing into irrigation water, by seed treatment or general application or dusting at the time when the pest has begun to appear or before the appearance of pests as a protective measure. For example, the modified insect protoxin protein of the invention may be mixed with grain to protect the grain during storage. It is generally important to obtain good control of pests in the early stages of plant growth, as this is the time when the plant can be most severely damaged. The compositions of the invention can conveniently contain another insecticide if this is thought necessary. In an embodiment of the invention, the composition is applied directly to the soil, at a time of planting, in granular form of a composition of a carrier. Another embodiment is a granular form of a composition comprising an agrochemical such as, for example, a herbicide, an insecticide, a fertilizer, or an inert carrier.

Compositions of the invention find use in protecting plants, seeds, and plant products in a variety of ways. For example, the compositions can be used in a method that involves placing an effective amount of the modified insect protoxin composition in the environment of the pest by a procedure selected from the group consisting of spraying, dusting, broadcasting, or seed coating.

Before plant propagation material (fruit, tuber, bulb, corm, grains, seed), but especially seed, is sold as a commercial product, it is customarily treated with a protectant coating comprising herbicides, insecticides, fungicides, bactericides, nematicides, molluscicides, or mixtures of several of these preparations, if desired together with further carriers, surfactants, or application-promoting adjuvants customarily employed in the art of formulation to provide protection against damage caused by bacterial, fungal, or animal pests. In order to treat the seed, the protectant coating may be applied to the seeds either by impregnating the tubers or grains with a liquid formulation or by coating them with a combined wet or dry formulation. In addition, in special cases, other methods of application to plants are possible, e.g., treatment directed at the buds or the fruit.

The plant seed of the invention comprising a DNA molecule comprising a nucleotide sequence encoding a modified protoxin protein of the invention may be treated with a seed protectant coating comprising a seed treatment compound, such as, for example, captan, carboxin, thiram, methalaxyl, pirimiphos-methyl, and others that are commonly used in seed treatment. In one embodiment within the scope of the invention, a seed protectant coating comprising a pesticidal composition of the invention is used alone or in combination with one of the seed protectant coatings customarily used in seed treatment.

The embodiments of the present invention may be effective against a variety of pests. For purposes of the present invention, pests include, but are not limited to, insects, fungi, bacteria, nematodes, acarids, protozoan pathogens, animal-parasitic liver flukes, and the like. Pests of particular interest are insect pests, particularly insect pests that cause significant damage to agricultural plants. "Insect pests" is intended to mean insects and other similar pests such as, for example, those of the order Acari including, but not limited to, mites and ticks. Insect pests of the present invention include, but are not limited to, insects of the order Lepidoptera, e.g. *Achoroia grisella, Acleris gloverana, Acleris variana, Adoxophyes orana, Agrotis epsilon, Alabama argillacea, Alsophila pometaria, Amyelois transitella, Anagasta kuehniella, Anarsia lineatella, Anisota senatoria, Antheraea pernyi, Anticarsia gemmatalis, Archips* sp., *Argyrotaenia* sp., *Athetis mindara, Bombyx mori, Bucculatrix thurberiella, Cadra cautella, Choristoneura* sp., *Cochylls hospes, Colias eurytheme, Corcyra cephalonica, Cydia latiferreanus, Cydia pomonella, Datana integerrima, Dendrolimus sibericus, Desmiafeneralis, Diaphania hyalinata, Diaphania nitidalis, Diatraea grandiosella, Diatraea saccharalis, Ennomos subsignaria, Eoreuma loftini, Esphestia elutella, Erannis tilaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americana, Helicoverpa subflexa, Helicoverpa zea, Heliothis virescens, Hemileuca oliviae, Homoeosoma electellum, Hyphantia cunea, Keiferia lycopersicella, Lambdinafiscellaria fiscellaria, Lambdinafiscellaria lugubrosa, Leucoma salicis, Lobesia botrana, Loxostege sticticalis, Lymantria dispar, Macalla thyrisalis, Malacosoma* sp., *Mamestra brassicae, Mamestra configurata, Manduca quinquemaculata, Manduca sexta, Maruca testulalis, Melanchra picta, Operophtera brumata, Orgyia* sp., *Ostrinia nubilalis, Paleacrita vernata, Papilio cresphontes, Pectinophora gossypiella, Phryganidia californica, Phyllonorycter blancardella, Pieris napi, Pieris rapae, Plathypena scabra, Platynota flouendana, Platynota stultana, Platyptilia carduidactyla, Plodia interpunctella, Plutella xylostella, Pontia protodice, Pseudaletia unipuncta, Pseudoplasia includens, Sabulodes aegrotata, Schizura concinna, Sitotroga cerealella, Spilonta ocellana, Spodoptera* sp., *Thaurnstopoea pityocampa, Tinsola bisselliella, Trichoplusia hi, Udea rubigalis, Xylomyges curiails*, and *Yponomeuta padella.*

Also, the embodiments of the invention may be effective against a variety of insect pests including insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, banded winged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean *thrips; Thrips tabaci*, onion *thrips; Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; chinch bug, e.g., *Blissus leucopterus leucopterus; Acrosternum hilare*, green stink bug; *Euschistus servus*, brown stink bug; *Jylemya platura*, seedcorn maggot; *Mayetiola destructor*, Hessian fly; *Petrobia latens*, brown wheat mite; Oil Seed Rape: *Vrevicoryne brassicae*, cabbage aphid; *Phyllotreta cruciferae*, crucifer flea beetle; *Phyllotreta striolata*, striped flea beetle; *Phyllotreta nemorum*, striped turnip flea beetle; *Meligethes aeneus*, rapeseed beetle; and the pollen beetles *Meligethes rufiranus, Meligethes nigrescens, Meligethes canadianus*, and *Meligethes viridescens*; Potato: *Leptinotarsa decemlineata*, Colorado potato beetle.

Furthermore, embodiments of the present invention may be effective against Hemiptera such as *Lygus hesperus, Lygus lineolaris, Lygus pratensis, Lygus rugulipennis* Popp, *Lygus pabulinus, Calocoris norvegicus, Orthops compestris, Plesiocoris rugicollis, Cyrtopeltis modestus, Cyrtopeltis notatus, Spanagonicus albofasciatus, Diaphnocoris chlorinonis, Labopidicola allii, Pseudatomoscelis seriatus, Adelphocoris rapidus, Poecilocapsus lineatus, Blissus leucopterus, Nysius ericae, Nysius raphanus, Euschistus servus, Nezara viridula, Eurygaster, Coreidae, Pyrrhocoridae, Timidae, Blostomatidae, Reduviidae*, and *Cimicidae*. Pests of interest also include *Araecerus fasciculatus*, coffee bean weevil; *Acanthoscelides obtectus*, bean weevil; *Bruchus rufimanus*, broadbean weevil; *Bruchus pisorum*, pea weevil; *Zabrotes subfasciatus*, Mexican bean weevil; *Diabrotica balteata*, banded cucumber beetle; *Cerotoma trifurcata*, bean leaf beetle; *Diabrotica virgifera*, Mexican corn rootworm; *Epitrix cucumeris*, potato flea beetle; *Chaetocnema confinis*, sweet potato flea beetle; *Hypera postica*, alfalfa weevil; *Anthonomus quadrigibbus*, apple curculio; *Sternechus paludatus*, bean stalk weevil; *Hypera brunnipennis*, Egyptian alfalfa weevil; *Sitophilus granaries*, granary weevil; *Craponius inaequalis*, grape curculio; *Sitophilus zeamais*, maize weevil; *Conotrachelus nenuphar*, plum curculio; *Euscepes postfaciatus*, West Indian sweet potato weevil; *Maladera castanea*, Asiatic garden beetle; *Rhizotrogus majalis*, European chafer; *Macrodactylus subspinosus*, rose chafer; *Tribolium confusum*, confused flour beetle; *Tenebrio obscurus*, dark mealworm; *Tribolium castaneum*, red flour beetle; *Tenebrio molitor*, yellow mealworm.

Nematodes include plant-parasitic nematodes such as root-knot, cyst, and lesion nematodes, including *Heterodera* and *Globodera* spp. such as *Globodera rostochiensis* and *Globodera pailida* (potato cyst nematodes); *Heterodera glycines* (soybean cyst nematode); *Heterodera schachtii* (beet cyst nematode); and *Heterodera avenae* (cereal cyst nematode).

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The above-defined terms are more fully defined by reference to the specification as a whole.

The following examples are presented by way of illustration, not by way of limitation.

EXPERIMENTAL

Example 1

Transformation of Maize and Regeneration of Transgenic Plants

The coding sequence for a full-length Cry8Bb1 protoxin (SEQ ID NO:5) is modified to comprise codons for a proteolytic activation site. Specifically, a DNA sequence encoding the FRRGFRRG (SEQ ID NO:6) proteolytic peptide is introduced in the junction between the N-terminal cystalline forming segment of the Cry8Bb1 protoxin and the C-terminal portion of the protoxin that comprises the active insect toxin upon cleavage. Immature maize embryos from greenhouse donor plants are bombarded with a plasmid containing the modified Cry8Bb1 protoxin nucleotide sequence operably linked to ubiquitin promoter and the selectable marker gene PAT (Wohlleben et al. (1988) *Gene* 70:25-37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the modified Cry8Bb1 protoxin nucleotide sequence described above, operably linked to a ubiquitin promoter, is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water

10 μl (1 μg) DNA in Tris EDTA buffer (1 μg total DNA)

100 μl 2.5 M $CaCl_2$

10 μl 0.1 M spermidine

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for expression of the modified Cry8Bb I protoxin by assays known in the art, such as, for example, immunoassays and western blotting.

Analysis of Transgenic Maize Plants

Transgenic maize plants positive for expression of the modified Cry8Bb1 protoxin are tested for resistance to WCRW using standard bioassays known in the art. Such methods include, for example, root excision bioassays and whole plant bioassays. See, e.g., U.S. Patent Publication No. US 2003/0120054 and International Publication No. WO 03/018810.

Bombardment and Culture Media Recipes

560Y Bombardment Medium 4.0 g/L N6 basal salts (SIGMA C-1416)
1.0 mL/L Eriksson's Vitamin Mix (1000×SIGMA-1511)
0.5 mg/L thiamine HCl
120.0 g/L sucrose
1.0 mg/L 2,4-D
2.88 g/L L-proline Ingredients are mixed and brought to volume with D-I $H_2O$ following adjustment to pH 5.8 with KOH. Gelrite is then added to a concentration of 2.0 g/L Gelrite and the medium is sterilized and cooled to room temperature. Finally, 8.5 mg/L silver nitrate is added.

560R Selection Medium 4.0 g/L N6 basal salts (SIGMA C-1416)
1.0 mL/L Eriksson's Vitamin Mix (1000×SIGMA-1511)
0.5 mg/L thiamine HCl
30.0 g/L sucrose
2.0 mg/L 2,4-D Ingredients are mixed and brought to volume with D-I $H_2O$ following adjustment to pH 5.8 with KOH. Gelrite is then added to a concentration of 3.0 g/L and the medium is sterilized and cooled to room temperature. Finally, 0.85 mg/L silver nitrate and 3.0 mg/L bialaphos are added.

288J Plant Regeneration Medium 4.3 g/L MS salts (GIBCO 11117-074)
5.0 mL/L MS vitamins stock solution (0.100 g nicotinic acid, 0.02 g/L thiamine HCL, 0.10 g/L pyridoxine HCl, and 0.40 g/L glycine brought to volume with polished D-1 $H_2O$) (Murashige and Skoog (1962) *Physiol. Plant.* 15:473)
100 mg/L myo-inositol
0.5 mg/L zeatin
60 g/L sucrose
1.0 mL/L 0.1 mM abscisic acid Ingredients are mixed and brought to volume with D-I $H_2O$ following adjustment to pH 5.6 with KOH. Gelrite is then added to a concentration of 3.0 g/L and the medium is sterilized and cooled to 60° C. Finally, 1.0 mg/L indoleacetic acid and 3.0 mg/L bialaphos are added.

Hormone-free Medium (272V)

4.3 g/L MS salts (GIBCO 11117-074)
5.0 mL/L MS vitamins stock solution (supra)
0.1 g/L myo-inositol
40.0 g/L sucrose Ingredients are mixed and brought to volume with D-I $H_2O$ following adjustment to pH 5.6 with KOH. Bacto-agar is then added to a concentration of 6.0 g/L and the medium is sterilized and cooled to 60° C.

Example 2

*Agrobacterium*-mediated Transformation of Maize and Regeneration of Transgenic Plants For *Agrobacterium*-mediated transformation of maize with the modified Cry8Bb1 protoxin nucleotide sequence of Example 1, the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the modified Cry8Bb1 protoxin nucleotide sequence to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). Optimally the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Optimally the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Optimally, the immature embryos are cultured on solid medium with a selective agent resulting in the selective growth of transformed cells. The callus is then regenerated into plants (step 5: the regeneration step), and calli grown on selective medium are cultured on solid medium to regenerate the plants. Transgenic maize plants positive for expression of the modified Cry8Bb1 protoxin are tested for resistance to WCRW, as described in Example 1.

Example 3

Proteolytic Cleavage of a Modified Insect Toxin in Transgenic Plants

The portion of the Cry8Bb1 loop between helix 3 and helix 4 of domain 1 of the insecticidal toxin, which has the sequence NGSR (SEQ ID NO: 7), was replaced by a protease cathepsin-L motif that has a sequence of FRRGFRRG (SEQ ID NO: 6). A construct containing this modified sequence was used to transform maize plants. Maize plants were transformed using the *Agrobacterium* protocol outlined in Example 2.

After transformation, transgenic maize plants expressing the modified Cry8Bb1 toxin protein were analyzed for the stability of the toxin molecule. Western analysis of the transgenic leaf and root tissues indicated that the toxin molecule generated in planta was cleaved by maize proteases into three fragments in the leaf and root tissues.

In order to characterize the cleavage sites, immunoprecipitation of the fragments using AminoLink (Pierce, Rockford Ill.) was initiated. The resulting fragments from the immunoprecipitation were separated by SDS-page electrophoresis and blotted into PVD membrane. Three protein bands of interest were cut and sequenced. The highest band fragment, which was also the least intense, indicated that the toxin molecule was intact. The sequence of the next fragment indicated that the toxin molecule was proteolytically cleaved in the plant, resulting in the removal of the first 49 amino acids. The lowest band sequence, which was also the most prevalent, showed that the toxin molecule was cleaved within the protease cathepsin-L motif FRRGFRRG (SEQ ID NO:6) at the last R.

The cleavage by maize root and leaf proteases of the modified Cry8Bb1 toxin molecule was primarily at this site. It was therefore concluded that maize proteases have high affinity for the protease motif FRRGFRRG (SEQ ID NO:6). Classical Cry proteins have a toxin domain and a crystal-forming domain. Only the toxin domain is needed for insecticidal activity. This motif was then introduced into the boundary of the toxin domain of Cry8Bb1 and its crystal-forming domain in order to obtain processing by plant proteases. The resulting cleavage at FRRGFRRG (SEQ ID NO:6) by plant proteases is expected to result in two protein products, the active toxin domain and the non-active crystal domain.

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

All publications, patents and patent applications mentioned in the specification are indicative of the level of those skilled in the art to which this invention pertains. All publications, patents and patent applications are herein incorporated by reference to the same extent as if each individual publication, patent or patent application was specifically and individually indicated to be incorporated by reference in its entirety.

Although the foregoing invention has been described in some detail by way of illustration and example for purposes of clarity of understanding, it will be obvious that certain changes and modifications may be practiced within the scope of the embodiments described herein.

That which is claimed:

1. An isolated nucleic acid molecule comprising a nucleotide sequence that encodes a polypeptide having proteolytic activity, wherein said nucleotide sequence is selected from the group consisting of:

(a) the nucleotide sequence set forth in SEQ ID NO:3;

(b) a nucleotide sequence encoding the amino acid sequence set forth in SEQ ID NO:4;

(c) a nucleotide sequence having at least 95% sequence identity to the nucleotide sequence set forth in SEQ ID NO:3; and (d) a nucleotide sequence encoding a polypeptide having at least 95% sequence identity to the amino acid sequence set forth in SEQ ID NO:4.

2. A vector comprising the nucleotide sequence of claim 1.

3. An expression cassette comprising the nucleotide sequence of claim 1 operably linked to a promoter that drives expression of the nucleotide sequence.

4. A host cell comprising a nucleotide sequence of claim 1.

5. A method for making a recombinant protein encoded by the polynucleotide of claim 1, wherein the method cultures the host cell of claim 4 under conditions in which the polypeptide is produced.

* * * * *